US009192782B1

(12) United States Patent
Grimm

(10) Patent No.: US 9,192,782 B1
(45) Date of Patent: Nov. 24, 2015

(54) SYSTEM AND METHOD FOR EVALUATING ACCEPTABLE DOSAGE RANGES FOR RADIATION TREATMENTS OF BODY TISSUE

(71) Applicant: Jimm Grimm, Huntingdon Valley, PA (US)

(72) Inventor: Jimm Grimm, Huntingdon Valley, PA (US)

(*) Notice: Subject to any disclaimer, the term of this patent is extended or adjusted under 35 U.S.C. 154(b) by 223 days.

(21) Appl. No.: 13/768,576

(22) Filed: Feb. 15, 2013

Related U.S. Application Data

(60) Provisional application No. 61/599,408, filed on Feb. 15, 2012.

(51) Int. Cl.
*A61N 5/10* (2006.01)

(52) U.S. Cl.
CPC ............. *A61N 5/1031* (2013.01); *A61N 5/1038* (2013.01); *A61N 5/1039* (2013.01); *A61N 2005/1041* (2013.01)

(58) Field of Classification Search
CPC ....... A61N 5/10; A61N 5/103; A61N 5/1031; A61N 2005/1041
USPC ............................................................ 600/1
See application file for complete search history.

(56) References Cited

U.S. PATENT DOCUMENTS

| | | | | |
|---|---|---|---|---|
| 2007/0276777 | A1* | 11/2007 | Krishnan et al. | 706/46 |
| 2010/0020931 | A1* | 1/2010 | Otto et al. | 378/65 |
| 2010/0054410 | A1* | 3/2010 | Nord et al. | 378/65 |
| 2010/0104068 | A1* | 4/2010 | Kilby et al. | 378/65 |

OTHER PUBLICATIONS

"External Radiation Therapy": http://web.archive.org/web/20100714204713/http://www.cancer.org/Treatment/TreatmentsandSideEffects/TreatmentTypes/Radiation/UnderstandingRadiationTherapyAGuideforPatientsandFamilies/understanding-radiation-therapy-external-radiation-therapy.*
Fowler, "21 years of Biologically Effective Dose," The British Journal of Radiology, 83 (2010), 554-568.*

* cited by examiner

*Primary Examiner* — Charles A Marmor, II
*Assistant Examiner* — Thaddeus Cox
(74) *Attorney, Agent, or Firm* — LaMorte & Associates, P.C.

(57) ABSTRACT

A system and method of producing a reference graph for use in selecting the proper radiation levels for use during radiation therapy. Using the radiation treatment plan, a physician can then create a dose volume histogram. The dose volume histogram is used to create a risk map for selected tissue. Data from one or more databases is then accessed and overlaid onto the risk map to create a reference graph. The data from the selected databases contains historical data of past radiation levels used during prior radiation therapies. Furthermore, the historical data can contain instances of adverse reactions due to high radiation levels. The physician can view the reference graph to determine if the radiation being used on a patient is either overly aggressive or overly safe in all areas of affected tissue.

18 Claims, 8 Drawing Sheets

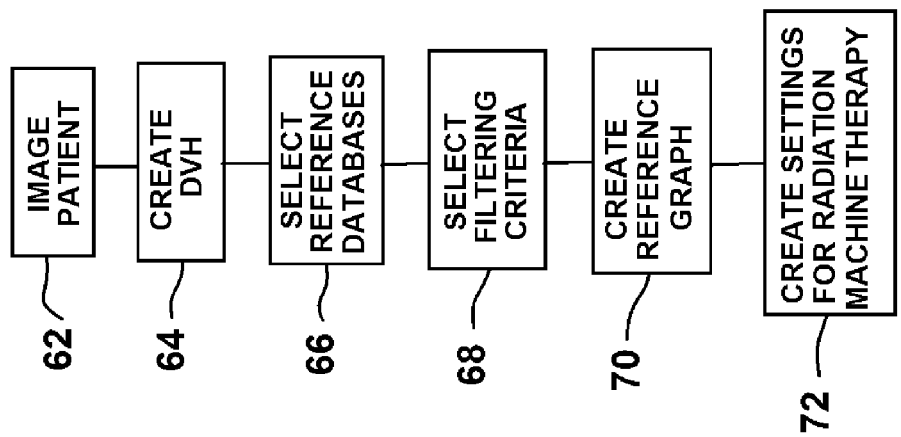

SYSTEM AND METHOD FOR EVALUATING ACCEPTABLE DOSAGE RANGES FOR RADIATION TREATMENTS OF BODY TISSUE

RELATED APPLICATIONS

The present application claims priority of U.S. Provisional Patent Application No. 61/599,408, entitled DVH Risk Map, filed Feb. 15, 2012.

BACKGROUND OF THE INVENTION

1. Field of the Invention

In general, the present invention relates to systems and methods that enable medical personnel to select the proper radiation dosage for the particular needs of a patient. More particularly, the present invention relates to software applications that graphically plot acceptable radiation dose ranges.

2. Prior Art Description

There are many medical conditions that can be treated with radiation therapy. However, one of the most important applications of radiation therapy is its use in treating cancer inside the body. If cancer cells can be located within the human body, then those cancer cells can be targeted with beams of radiation. The radiation carries enough energy to kill the cancer cells as the radiation impinges upon the cancer cells. In this manner, cancer cells can be killed deep within tissue masses without the need for surgery.

The radiation beams begin at different physical points. Each individual radiation beam has a low dose that is insufficient to damage cells by itself. In this manner, the beams of radiation can reach the cancer cells without damaging healthy tissue along the path. The multiple beams of radiation all converge at the point of the cancer cells. The combined dose from the multiple beams of radiation then becomes sufficient to kill the cancer cells.

A problem associated with radiation therapy is that the level of radiation increases as the beams of radiation approach the treatment area. Consequently, the tissue surrounding the tumor is subjected to significant levels of radiation. Likewise, the tissue along each path of the radiation beams is also subjected to some radiation dose.

No two cancers are alike. Each cancer patient has cancer cells that are unique in location and mass to that patient. As such, the best way to direct beams of radiation onto cancer cells has become a complicated science. Physicians and dosimetrists must determine where to position the beams of radiation during radiation therapy in order to have the maximum effect on the cancer cells and the minimal effect on surrounding healthy tissue. Doctors and dosimetrists also try to avoid radiation dose to critical organ tissue, provided that tissue is healthy.

In the prior art, the manner in which a physician or dosimetrist plans a course of radiation therapy is a three step process. In the first step, the physician pinpoints the exact location of the cancer cells to be targeted. This is traditionally done using three-dimensional body imaging equipment, such as an MRI scan, a CAT scan, a PET scan or the like. Once the physician locates the target cancer cells, the dosimetrist develops a treatment plan and a dose volume histogram (DVH). The development of the dose volume histogram is the second step. The physician utilizes the dose volume histograms to evaluate the dose distribution of tissue in and around the targeted cancer cells. The dosimetrist can alter the dose, position, and direction of the various radiation beams to develop a plan that will kill the targeted cancer cells, yet minimize dose to surrounding tissue, especially critical organ tissue. In the last step, the radiation equipment is programmed to the settings developed using the treatment plan. The equipment is then ready for use on the patient.

In the prior art, the total dose of radiation is divided into a number of fractional doses, to be delivered on a daily or weekly basis. The number of fractions is defined as the number of partial treatments the patient will receive. The maximum tolerated total dose is a nonlinear function of the number of fractions. When the number of fractions is large, like 25 or 40, a higher total dose can be used than if the number of fractions is small like 1 or 5. Conversely, a large dose per fraction can obliterate certain tumors, but then the number of fractions would need to be small. Part of the problem associated with prior art techniques is that a systematic way of visualizing treatment outcomes as a function of the number of fractions is needed.

Furthermore, such prior art techniques do not have facility to overlay information from historical treatment outcomes onto the current treatment plan to help evaluate the risk associated with the dose to critical structures.

A need therefore exists for a system and method that can assist a physician and dosimetrist in optimizing the radiation therapy dose distribution to maximize effectiveness while minimizing collateral radiation dosage. A need also exists for a system and method that can actively inform a physician and/or dosimetrist that the settings selected for the radiation therapy surpass safe levels for any region of healthy tissue along the various radiation beam paths. These needs are met by the present invention as described and claimed below.

SUMMARY OF THE INVENTION

The present invention is a system and method of producing a reference graph for use in selecting the proper radiation levels for use during radiation therapy. A physician or dosimetrist references a three-dimensional scan of tissue in a patient's body. The physician or dosimetrist then creates a radiation treatment plan for the scanned tissue. Using the radiation treatment plan, the physician, or dosimetrist can then create an initial dose volume histogram by plotting tissue volume versus a range of possible radiation levels that can be used during course of radiation therapy.

From the dose volume histogram, the present invention extracts a dose value corresponding to a region (P) in the patient. This dose value is plotted versus the number of fractions as the basis for the DVH Risk Map. Data from one or more databases is then accessed and overlaid onto the DVH Risk Map to create a reference graph. The data from the selected databases contains historical data of past radiation levels used during prior radiation therapies. Furthermore, the historical data can contain instances of adverse reactions due to high radiation levels. The physician or dosimetrist can view the reference graph to determine if the radiation being used on a patient is either overly aggressive or overly safe in all areas of affected tissue.

BRIEF DESCRIPTION OF THE DRAWINGS

For a better understanding of the present invention, reference is made to the following description of an exemplary embodiment thereof, considered in conjunction with the accompanying drawings, in which:

FIG. 8 is a block diagram logic flow showing the operating method of the present invention.

DETAILED DESCRIPTION OF THE DRAWINGS

Although the present invention system and method can be used in the treatment of lung cancer, pancreatic cancer, breast cancer, and many other cancers, the exemplary embodiment illustrated shows the system being used to determine the proper radiation treatment plan for treating an unnamed mass of "tissue". This generic embodiment is selected in order to set forth an example that best illustrates the system and method of the invention. The illustrated embodiment, however, is merely exemplary and should not be considered a limitation when interpreting the scope of the appended claims.

Figure 1:
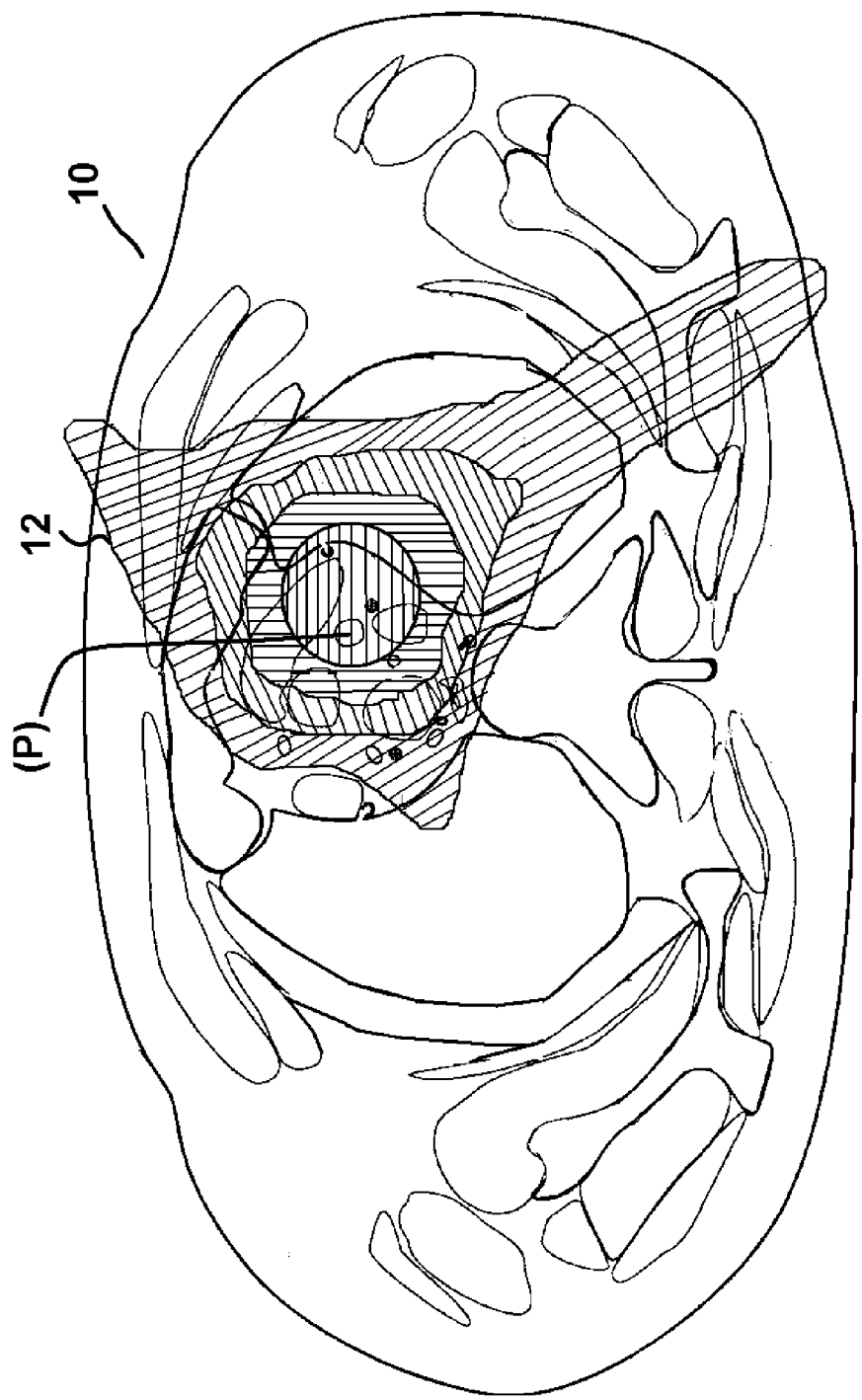
FIG. 1 is a prior art image of scanned body tissue having a radiation treatment plan superimposed over the scanned image.

Referring to FIG. 1, an image 10 available from prior art systems is shown. The image 10 shows a section of the human body imaged by an imaging machine, such as an MRI scan, CAT scan or PET scan imager. Superimposed upon the image 10 is a radiation treatment plan 12. The radiation treatment plan 12 indicates the radiation dose levels to various tissue areas within the body for some predetermined operation settings of a radiation therapy machine. The image of FIG. 1 can be generated using available commercial software. Such prior art software also enables a physician or dosimetrist to select any one region (P) on the image 10. From all such regions (P) for a selected anatomical structure, a dose volume histogram can be produced. The dose volume histogram is a plot of tissue volume versus radiation dose, or alternatively, a plot of radiation dose versus tissue volume. The dose volume histogram can be expressed as a plot of $\vec{x}$, $\vec{y}$, where $\vec{x}$ is a vector of the range of doses in the plan, from the minimum dose to the maximum dose, and $\vec{y}$ is the corresponding vector of the volumes of the anatomical structure receiving each particular dose. The dose $\vec{x}$ and the volume $\vec{y}$ may be expressed in any applicable units, either absolute units or in normalized relative units.

Figure 2:
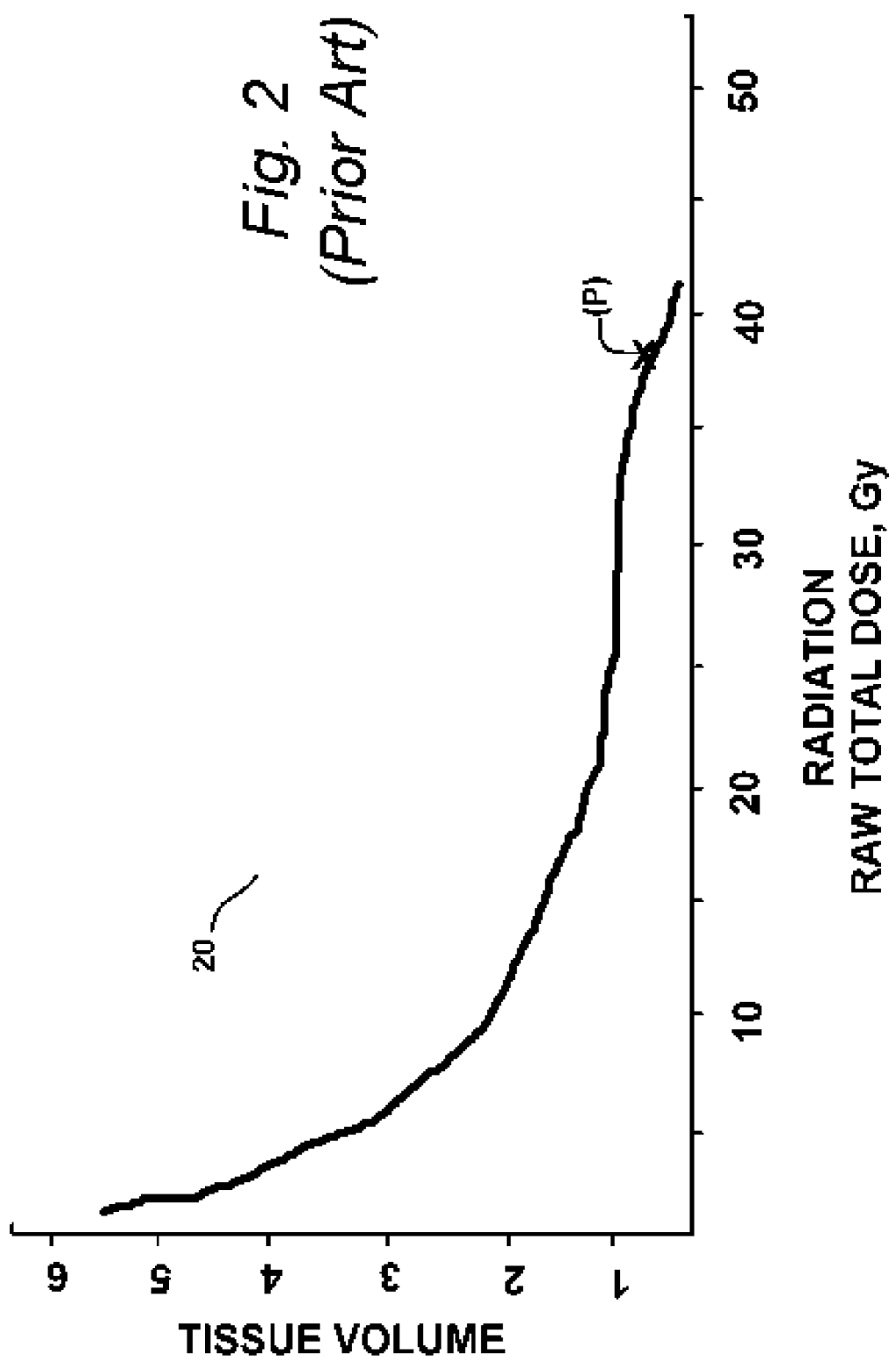
FIG. 2 is a prior art dose volume histogram including a dose value corresponding to region (P) shown in FIG. 1.

Referring to FIG. 2 in conjunction with FIG. 1, an example of a dose volume histogram 20 is shown for a physician who selected region (P) in the image 10 of FIG. 1. As can be seen, the dose volume histogram 20 plots tissue volume versus Raw Total Dose Gy.

Figure 3:
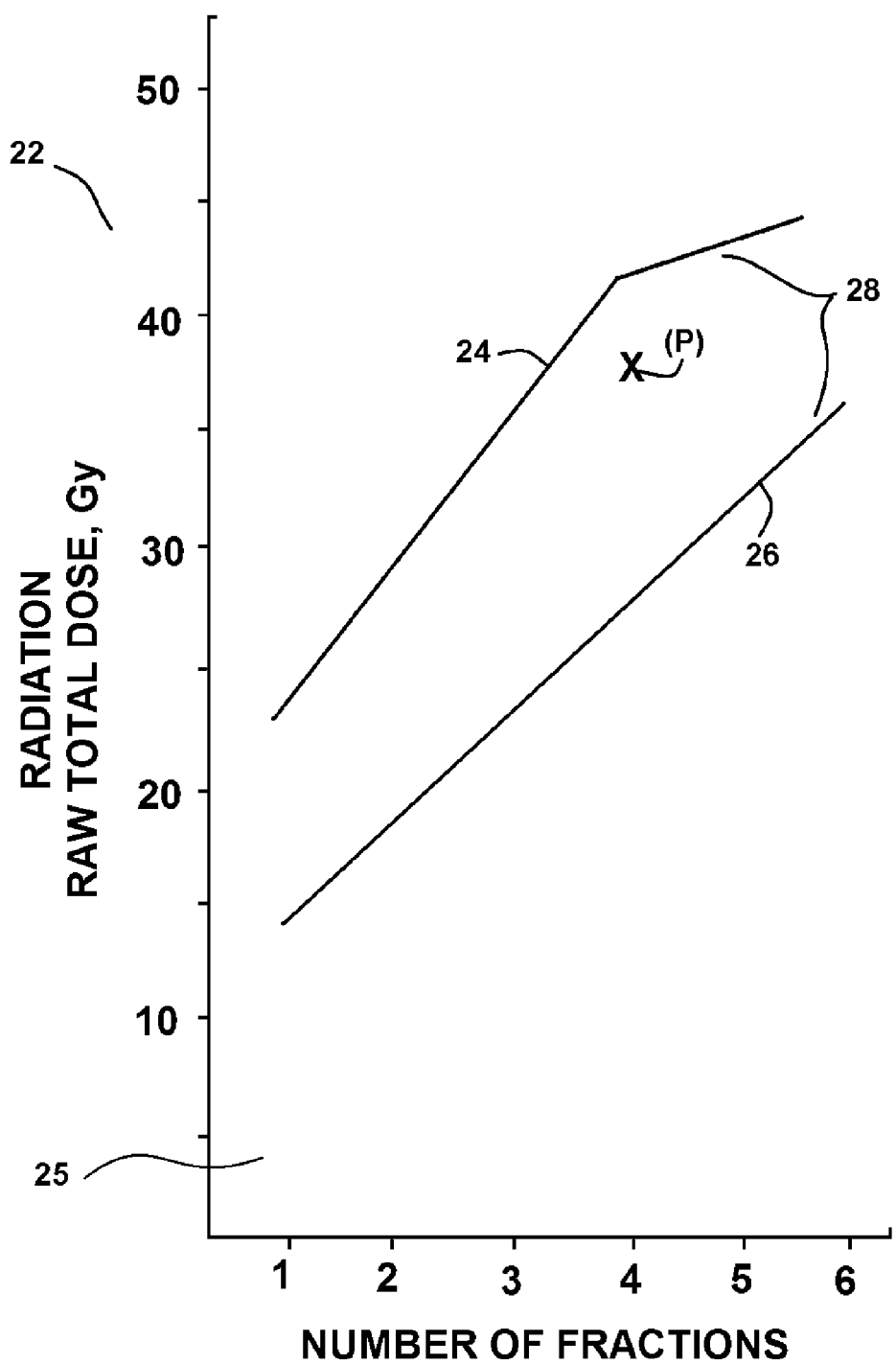
FIG. 3 is a reference graph containing high and low thresholds overlaid upon a dose value corresponding to region (P)

Referring now to FIG. 3, the initial workings of the present invention system and method are shown as they operate to produce a useful reference graph 22, which consists of certain points determined from dose volume histograms and arranged in a the following manner. In FIG. 3, the dose values corresponding to selected regions in the patient are determined from the initial dose volume histogram 20 of FIG. 2 and plotted versus fractions rather than the raw total dose of FIG. 2. This new plotting is herein referred to as a DVH Risk Map 25. An initial high-risk threshold 24 and low-risk threshold 26 are shown. In general, the initial high-risk threshold 24 is indicative of dose levels over which would be considered more harmful than helpful for the tissue region (P) selected. Conversely, the initial low-risk threshold 26 is indicative of dose levels that statistically cause no harm to the selected tissue. A marginal range 28 is interposed between the high-risk threshold 24 and the low-risk threshold 26. As such, a physician wants the radiation levels near or below the low-risk threshold 26 for most tissue outside the target zone of the cancer cells.

The physician can select different formats for the high-risk threshold 24 and the low-risk threshold 26. The first format choice indicates if volume $Y_A$ of the selected tissue area exceeds dose $X_A$. The second format choice indicates if only a certain percentage $Y_B$ of the selected tissue area exceeds dose $X_B$. The third format choice indicates if any tissue volume $Y_C=0$ (zero) of the selected tissue area exceeds dose $X_C$. This third format choice specifies that the maximum dose of the specified structure may not exceed dose $X_C$. In all three formats, only $Y_i$ of a selected tissue sample may exceed dose $X_i$, where i is chosen from the three format sets and the units of $Y_i$ are volume or percent, and the unit of $X_i$ is dose.

The high-risk threshold 24 and the low-risk threshold 26 are determined using currently accepted radiobiological standards for dose levels to various types of body tissue.

Figure 4:
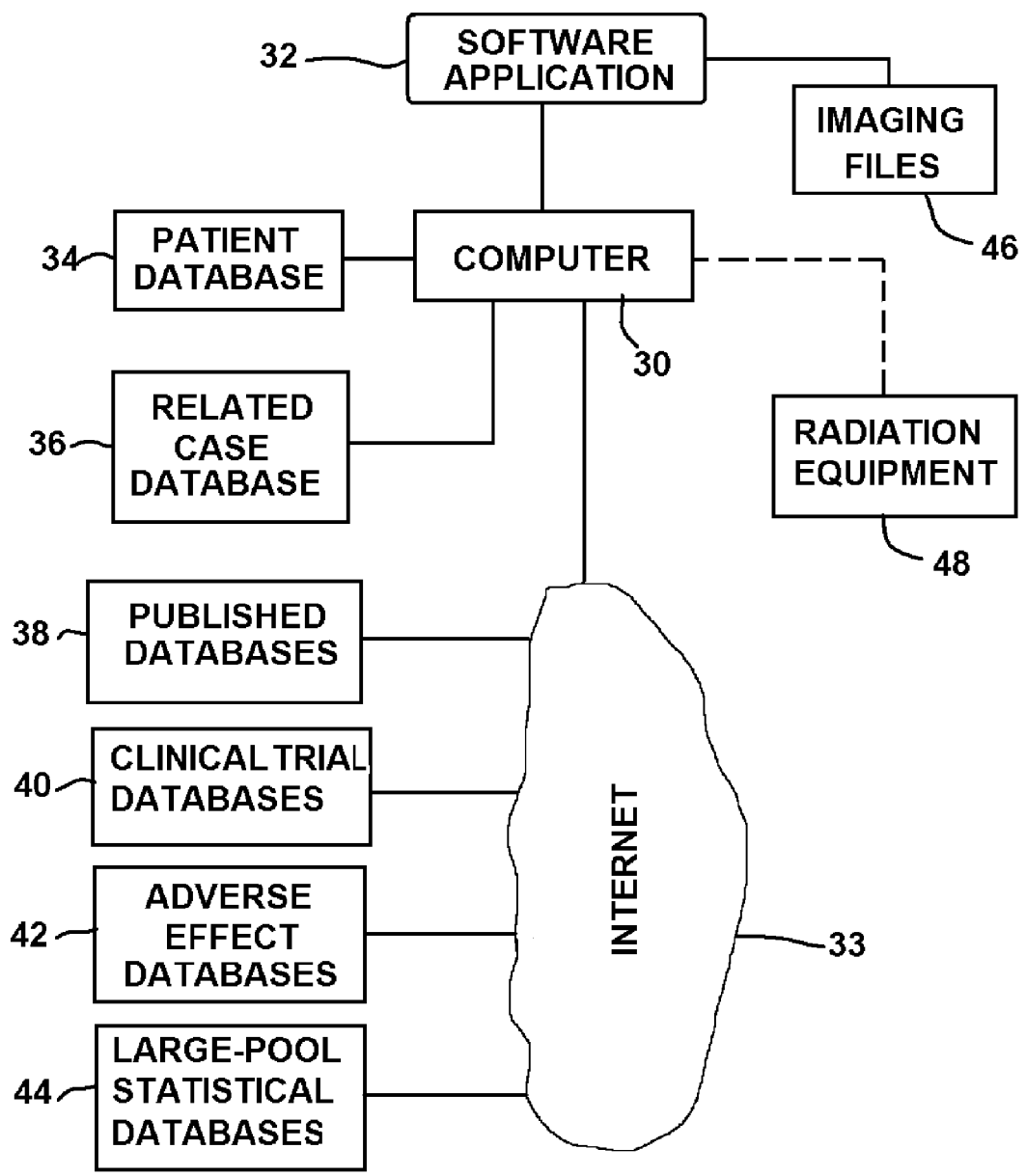
FIG. 4 is a flow chart showing the primary components of the present invention system.

Referring to FIG. 4, it will be understood that the reference graph 22 can be further modified by overlaying more information onto the DVH Risk Map 25 of FIG. 3. In FIG. 4, it can be seen that the system and method requires a computer 30 that runs the software application 32 of the present invention. The computer 30 has access to various resource databases, either directly or through a network connection, such as the Internet 33. The first resource database 34 contains the radiobiological treatment records of the patient being treated. This database 34 contains the radiation treatment plan doses and outcomes previously experienced by other patients. The outcomes data in this database 34 indicates if the subject patients had any adverse effects from radiation treatments.

The second resource database 36 contains data from practice related cases; this is data from other patients in the physician's practice. Preferably, the data contains information from patients that are being treated with the same radiation equipment as is the current subject patient. In this manner, the related case database 36 contains information indicative of the nuances of the radiation equipment being used and the preferences of the attending physician. The related case database 36 will also contain instances of adverse effects experienced by other patients at various radiation doses.

The data contained within the related case database 36 can be filtered to best match the subject patient. For example, if the subject patient being treated is a middle-aged male, data regarding females, adolescents, and geriatrics can be filtered from use.

The medical records of the subject patient and the medical records of related cases are both maintained and updated by the physician's office. However, this data may or may not be statistically significant depending upon many factors. Those factors include the age and size of the physician's practice, the age of the radiation equipment, and the number of times specific pieces of radiation equipment have been used.

Optional outside databases may also be accessed. For instance, many dose tolerance limits for various tissue types are periodically published in medical journals and technical papers. A database 38 for published dose tolerance limits can be accessed.

Likewise, there are many ongoing radiobiological studies that monitor and track the effects of various dose limits on various tissue types. Clinical trial databases 40 containing such test validated dose limits can be accessed.

Adverse effect databases 42 also exist that collect data from doses that caused adverse effects on patients. Databases 42 containing such outcomes data can be accessed.

Lastly, data collected by different practices, physicians and hospitals can be shared to create a large-pool statistically reliable database 44 containing actual data from many patients. Such large-pool databases 44 can be accessed.

The software application 32 enables data from all outside databases to be filtered. The data can be filtered by patient type, tissue type, cancer type, treatment equipment type, and so forth, to best match the situation and demographics of a particular patient.

The computer 30 running the software application 32 of the present invention can also be linked to imaging files 46 that contain the imaging data shown in FIG. 1 and the dose volume histogram data of FIG. 2. Depending upon selected inputs by a physician, the software application 32 will generate settings to be used by radiation equipment 48 used during the radiation therapy.

Figure 5:
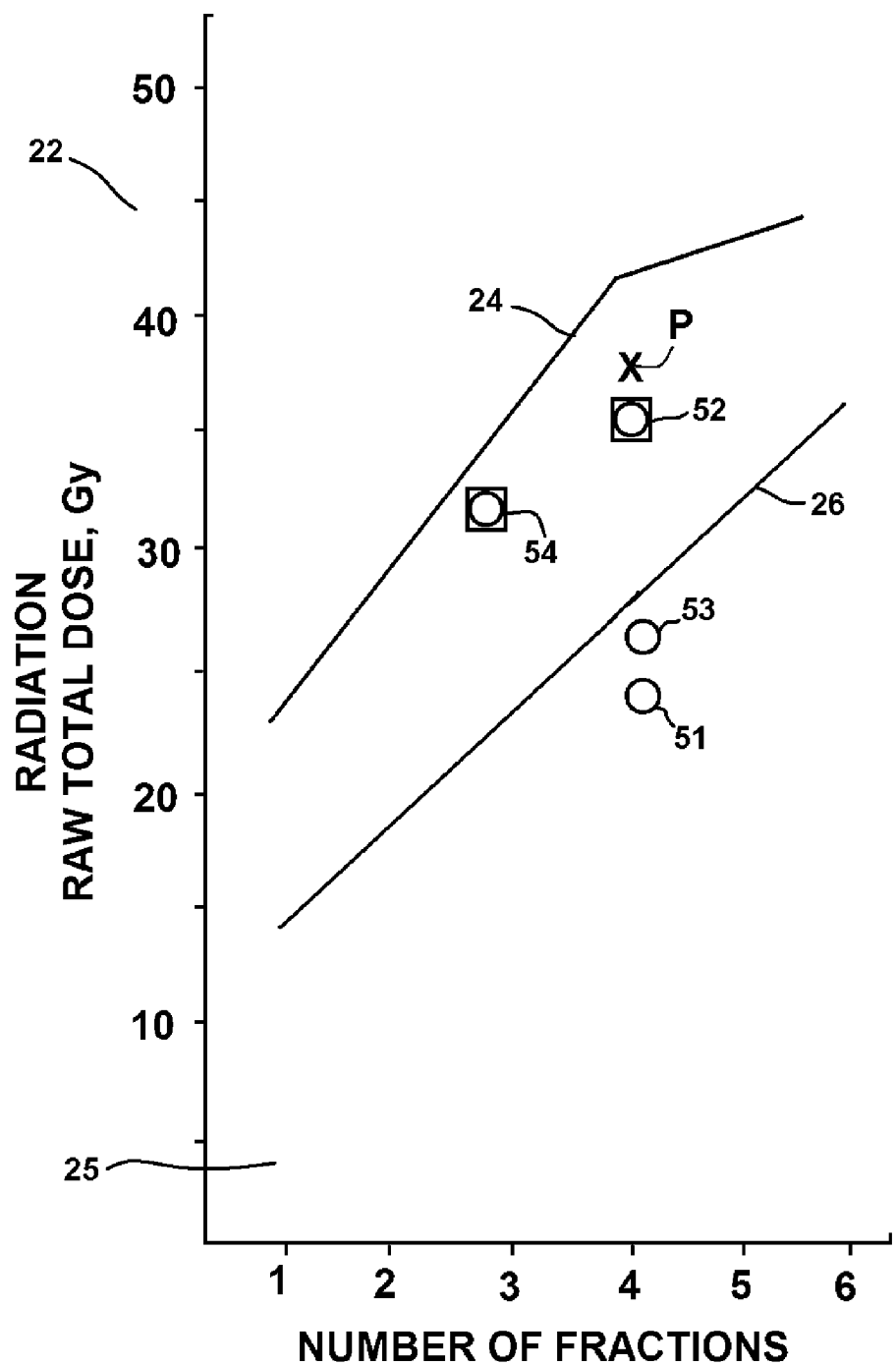
FIG. 5 is a reference graph having patient data overlaid upon a dose value corresponding to region (P)

Referring now to FIG. 5 in conjunction with FIG. 4, a further overlay of information is added to the reference graph 22. In FIG. 5, the data from the patient's database 34 is used in the overlay. As is indicated in the reference graph 22, the patient has received four previous radiation treatments 51, 52, 53, 54. Two of the treatments 51, 53 were below the low risk threshold 26. Two of the treatments were in the moderate risk zone 28 between the low-risk threshold 26 and the high-risk threshold 24. The highest of the prior received dosages 53, 54 caused an adverse reaction. This is indicated by the square surrounding the data entry.

Using the reference graph 22, a physician can quickly ascertain that the dosage of the next treatment should be altered so that it falls below the dosage level that caused the adverse reaction. This effectively lowers the high-risk threshold 24 for the subject patient. The information is graphically conveyed to the physician and can be instantly recognized by glancing at the reference graph 22.

Figure 6:
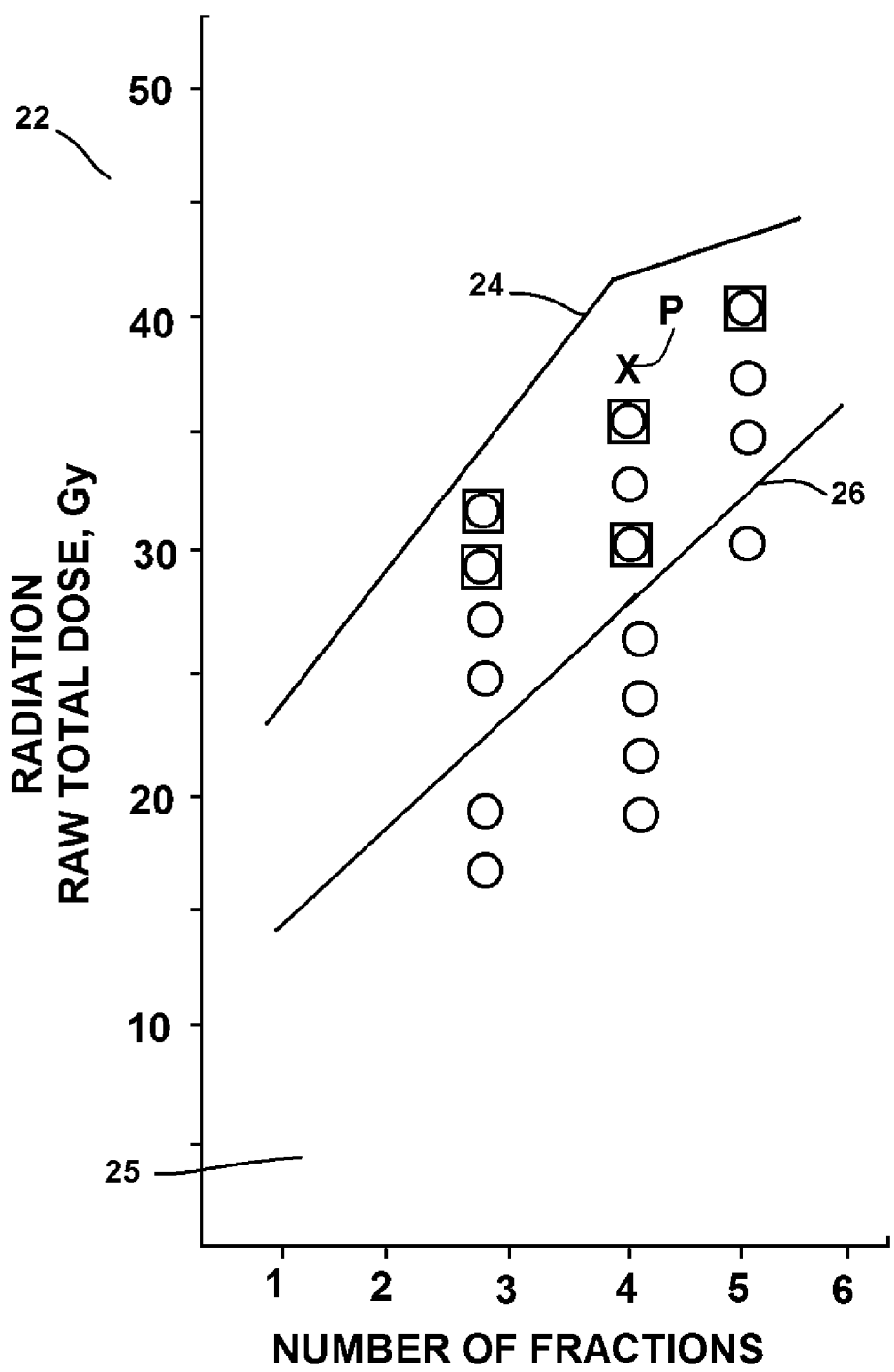
FIG. 6 is a reference graph having related case data overlaid upon a dose value corresponding to region (P)

Referring to FIG. 6 in conjunction with FIG. 4, a reference graph 22 is shown that uses the data from the related case database 36. This reference graph 22 can be used if the patient does not have any statistically significant prior treatment history.

The data from the related case database 36 is filtered to match the demographics and other specifics of the subject patient. For example, suppose the subject patient is being treated in hospital A by radiation machine B. The data in the related case database 36 can be filtered to match this location and equipment. The data from the related case database 36 can then be further filtered to match the weight, age, gender, ethnicity, and so forth of the patient. The filtered data is then overlaid on a DVH Risk Map to produce the reference graph 22.

As is indicated in the reference graph 22, many of the treatments are below the low-risk threshold 26. Conversely, about a half of the treatments are above the moderate risk zone 28 between the low risk threshold 26 and the high-risk threshold 24. A few of the higher dosages caused an adverse reaction. This is indicated by the square surrounding the data entry.

Figure 7:
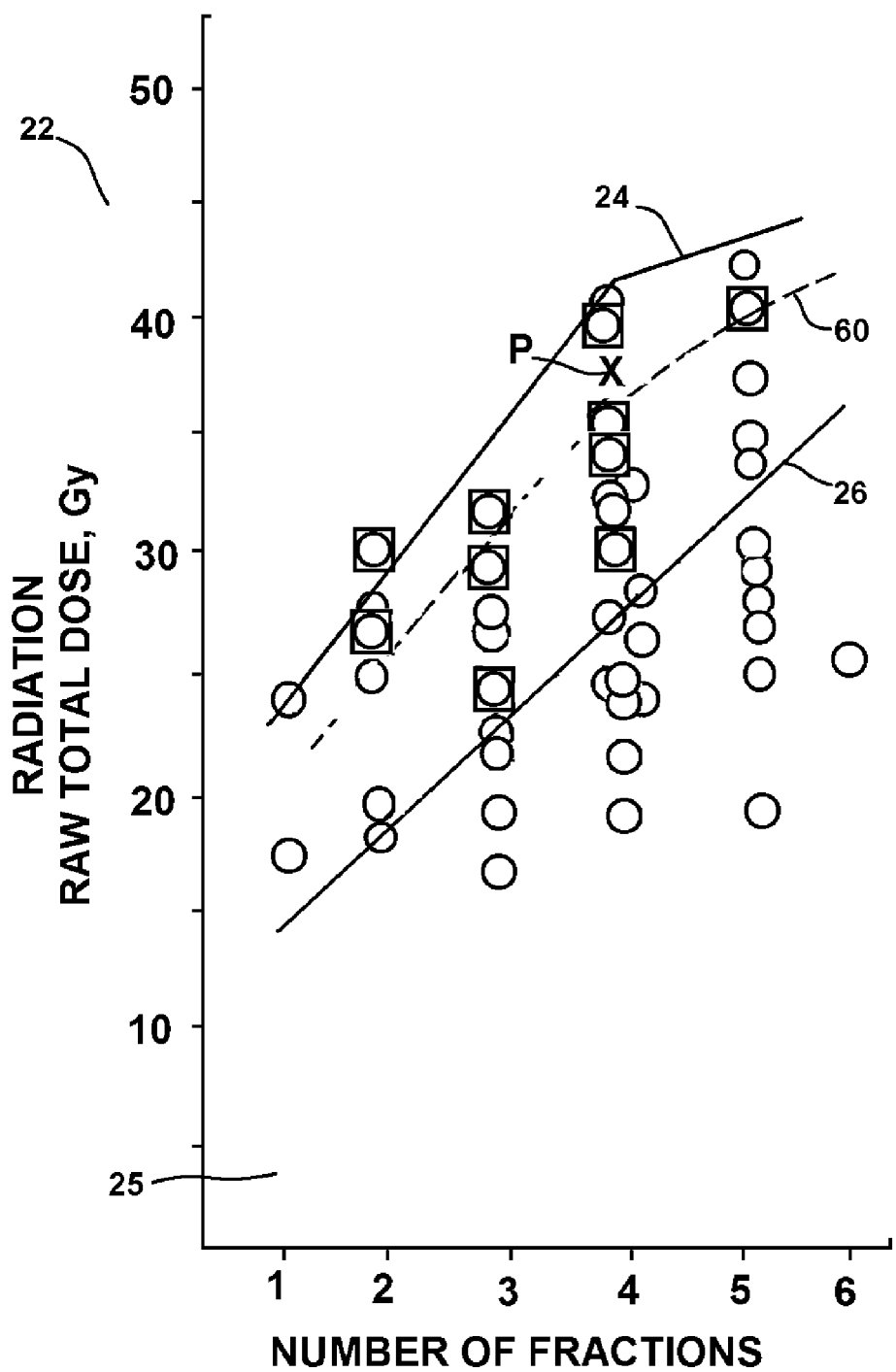
FIG. 7 is a reference graph having public data overlaid upon a dose value corresponding to region (P)

Referring to FIG. 7 in conjunction with FIG. 4, a reference graph 22 is shown that uses the data from one or more of the outside database 38, 40, 42, 44. These databases 38, 40, 42, 44 can be used if the patient's file database 34 and the related case database 36 lack statistically significant data.

The data from the outside databases 38, 40, 42, 44 are filtered to match the patient's demographics and the radiation equipment 48 being used. The filtered data is then overlaid on the DVH Risk Map to produce the reference graph 22.

As is indicated in the reference graph 22, many of the treatments are below the low-risk threshold 26. Conversely, some of the treatments are above the high-risk threshold. Most of the treatments are in the moderate risk zone 28 between the low risk threshold 26 and the high-risk threshold 24. A few of the dosages caused an adverse reaction. The data for adverse reactions can be averaged and plotted, as is indicated by average reaction line 60.

Using the reference graph 22, a physician can quickly ascertain that the dosage of the next treatment should be altered so that it falls below the average reaction line 60 that causes, on average, an adverse reaction to the demographic represented by the filtered data.

The data points from different databases can be identified by different plot icons in order to minimize confusion. By using all available data, a physician can determine how the dosage levels selected for a particular patient relate to national statistics. A physician can also ascertain if a patient has a higher or lower tolerance to radiation than does the average patient. In this manner, a physician can craft a more or less aggressive approach.

Referring lastly to FIG. 8, in conjunction with all previous figures, the method of operation for the present invention can now be explained. As is indicated by Block 62 and Block 64, a patient is imaged and a basic initial dose volume histogram is developed using prior art equipment and techniques. Using the software application 32 of the present invention, one or more reference databases 34, 36, 38, 40, 42, 44 are selected. See Block 66. As is indicated, the databases can include a database 34 containing the patient's records, a database containing related case data 36, and databases 38, 40, 42, 44 containing data accumulated from outside sources.

The physician selects one or more of the databases 34, 36, 38, 40, 42, 44 for use. The physician then selects filter criteria to filter the data from the selected databases. See Block 68. The filter criteria can include the demographics of the patient, the tissue type, the cancer type, and or the radiation equipment in use. The software application 32 then creates a reference graph 22. In the reference graph 22, the high-risk threshold 24 and the low risk threshold 26 are plotted. These trends are plotted using approved radiation dosage protocols. The filtered data from the selected databases is then overlaid onto the DVH Risk Map to create the reference graph 22. See Block 70. Instances of adverse effects are graphically identified on the reference graph 22.

By viewing the reference graph 22, a physician can better and more rapidly determine radiation dosages to be used on the patient. The selected radiation doses are then saved to initialize a radiation therapy machine for the next course of radiation therapy. See Block 72.

It will be understood that the embodiments of the present invention that are illustrated and described are merely exemplary and that a person skilled in the art can make many variations to those embodiments. For instance, the appearance of the reference graph and the icons of the overlays can be changed in many ways. All such embodiments are intended to be included within the scope of the present invention as defined by the claims.

What is claimed is:

1. A method of determining radiation levels for use during radiation therapy for a subject patient, said method comprising the steps of:

utilizing an imaging machine to identify a volume of tissue within said subject patient to be affected by said radiation therapy, wherein said volume of tissue contains a tissue region;
determining a radiation dose value corresponding to said tissue region in said patient;
providing a computer having access to reference databases;
utilizing said computer to generate an initial graph by plotting radiation dose values versus a range of possible fractions into which said radiation therapy can be divided;
utilizing said computer to overlay said radiation dose value onto said initial graph;
utilizing said computer to retrieve historical data from at least one of said reference databases, wherein said historical data includes past radiation levels used during prior radiation therapies;
utilizing said computer to overlay historical data onto said initial graph, therein providing a reference graph to assist in selecting an effective radiation level for said volume of tissue of said subject patient.

2. The method according to claim 1, wherein said historical data contains indicators of adverse effects caused by said past radiation levels at different fractions.

3. The method according to claim 2, wherein said historical data contains radiation levels at different fractions used in the past on said subject patient.

4. The method according to claim 2, wherein said radiation therapy is to be performed by a particular radiation machine and said historical data contains radiation levels at different fractions used in the past on said particular radiation machine.

5. The method according to claim 2, wherein said historical data contains radiation levels at different fractions published in medical journals.

6. The method according to claim 2, wherein said historical data contains radiation levels at different fractions utilized in clinical trials.

7. The method according to claim 2, further including the step of plotting a maximum radiation dose threshold level onto said reference graph.

8. The method according to claim 7, further including the step of plotting a minimum radiation dose threshold level onto said reference graph.

9. A method of producing a reference graph for use in selecting radiation levels to be used during radiation therapy for a subject patient, said method comprising the steps of:
utilizing an imaging machine to identify a volume of tissue within said subject patient to be affected by said radiation therapy;
determining a radiation dose value corresponding to said tissue region in said patient;
providing a computer having access to reference databases;
utilizing said computer to generate an initial graph by plotting radiation dose values used during said radiation therapy versus a range of possible fractions into which said radiation therapy can be divided;
utilizing said computer to overlay said radiation dose value onto said initial graph;
utilizing said computer to overlay high and low radiation dose threshold levels onto said initial graph, therein creating a reference graph to assist in selecting an effective radiation level for said volume of tissue within said subject patient.

10. The method according to claim 9, further including the step retrieving radiation levels from at least one of said reference databases that were found to cause adverse effects when treating similar volumes of tissue in the past, and utilizing said computer to overlay said radiation levels onto said reference graph.

11. The method according to claim 10, further including the step of retrieving historical data from at least one of said reference databases, wherein said historical data includes past radiation levels and fractions used during prior radiation therapies, and utilizing said computer to overlay said radiation levels onto said reference graph.

12. The method according to claim 11, wherein said radiation therapy is to be conducted by a physician and said historical data contains radiation levels and fractions used in the past by said physician.

13. The method according to claim 11, wherein said historical data contains radiation levels and fractions published in medical journals.

14. The method according to claim 11, wherein said historical data contains radiation levels and fractions utilized in clinical trials.

15. A method of determining radiation levels for use during radiation therapy for a subject patient, wherein the subject patient has a subject demographic, and wherein the radiation therapy is to be performed on a particular radiation machine, said method comprising the steps of:
utilizing an imaging machine to identify a volume of tissue within said subject patient to be affected by said radiation therapy;
determining a radiation dose value corresponding to said tissue region in said patient;
providing a computer having access to reference databases;
utilizing said computer to generate an initial graph that plots radiation dose values used during said radiation therapy versus a range of possible fractions into which said radiation therapy can be divided;
utilizing said computer to access at least one of said reference databases containing historical data of radiation doses used during prior radiation therapies;
utilizing said computer to filter said historical data for data that matches said subject demographic of said subject patient, therein producing filtered data; and
utilizing said computer to plot at least some of said filtered data onto said initial graph, therein providing a reference graph to assist in selecting an effective radiation level for said volume of tissue of said subject patient.

16. The method according to claim 15, wherein said filtered data contains indicators of adverse effects caused by past radiation levels.

17. The method according to claim 15, further including the step of utilizing said computer to plot a maximum radiation dose threshold level onto said reference graph.

18. The method according to claim 17, further including the step of utilizing said computer to plot a minimum radiation dose threshold level onto said reference graph.

* * * * *